Oct. 29, 1963 D. H. MOREY, JR Plant Pat. 2,292
ROSE PLANT
Filed Sept. 18, 1962
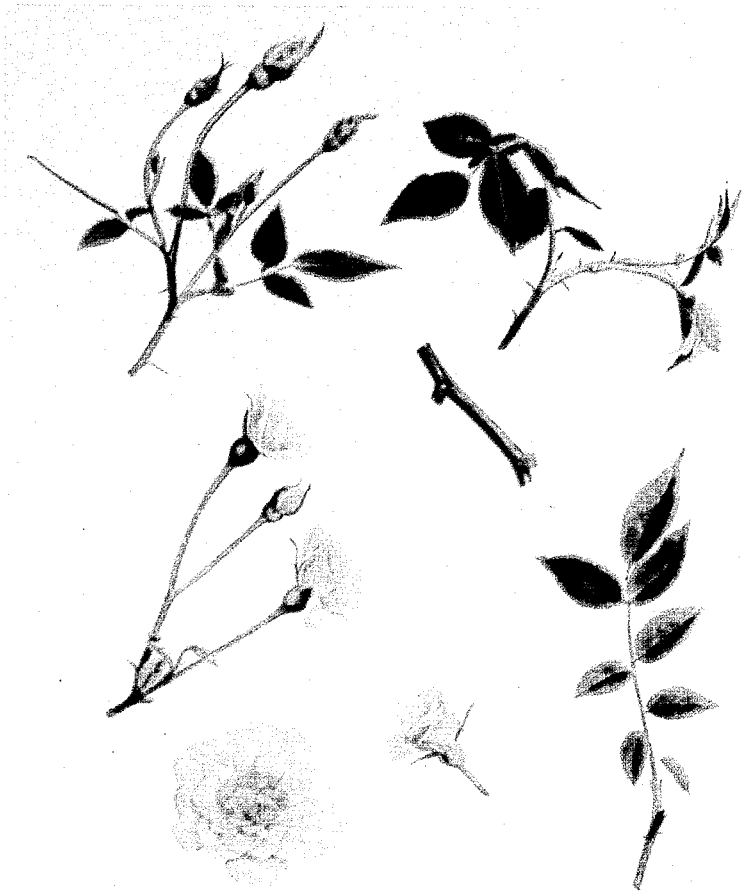
Inventor.
Dennison H. Morey, Jr
By: Robb & Robb
Attorneys.

United States Patent Office

Plant Pat. 2,292
Patented Oct. 29, 1963

2,292
ROSE PLANT

Dennison H. Morey, Jr., Pleasanton, Calif., assignor to Jackson & Perkins Company, Newark, N.Y., a corporation of New York Filed Sept. 18, 1962, Ser. No. 224,585
1 Claim. (Cl. Plt.—9)

The present invention relates to a new and distinct variety of rose plant of the miniature class, which was originated by me by crossing the variety "Mother's Day" (unpatented) with the variety "Rosy Jewel" (Plant Patent No. 1,899).

The primary objective of this breeding was to produce a new rose variety of the miniature class which bears flowers of a new color not heretofore present in existing miniature roses. This objective was fully achieved, along with other desirable improvements, as evidenced by the following unique combination of characteristics which are outstanding in the new variety and which distinguish it from its parents, as well as from all other varieties of which I am aware:

(1) A compact and miniature habit of plant growth ranging in height from 8 to 10 inches;

(2) Attractive foliage of Kildare Green color; and (3) A distinctive and attractive general color tonality of the flowers corresponding to Thulite Pink.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Mother's Day."
*Pollen parent.*—"Rosy Jewel."

Classification:
*Bontanic.*—Miniature.
*Commercial.*—Miniature.

*Flower*

(Observations made from specimens grown outdoors at Newark, New York, during the latter part of the month of August.)

Blooming habit: Recurrent—continuous.

Bud:
*Size.*—Small.
*Form.*—Ovoid; is not affected by wet or hot weather.
*Color.*—When sepals first divide—Spinel Pink, Plate 26. When petals begin to unfurl—Thulite Pink, Plate 26. When half-blown: inside of petals—Hermosa Pink, Plate 1, lightly overcast with Thulite Pink, Plate 26; reverse of petals—Venetian Pink, Plate 13, lightly overcast with La France Pink, Plate 1.
*Sepals.*—Slightly branched; curl back when petals begin to unfurl. Color: inside—Light Turtle Green, Plate 32; outside—Light Bice Green, Plate 17.
*Calyx.*—Color—Light Bice Green, Plate 17. Shape—apple. Size—small. Aspect—smooth. Odor when rubbed—none.
*Peduncle.* — Length — short. Aspect — smooth. Strength—erect; slender. Color—Light Cress Green, Plate 31.
*Opening.*—Opens up well, is not effected by adverse weather conditions.

Bloom:
*Size.*—Small. Average size when fully expanded—1 inch.
*Borne.*—Several together and in clusters.
*Stems.*—Short; strong.
*Form (when first open).*—Open. Permanence—retains its form to the end, but outer petals curl back.
*Petalage.*—Double (full but open center). Number of petals under normal conditions—from 40 to 50.
*Color.*—Center of flower—Thulite Pink, Plate 26, very lightly overcast with Eugenia Red, Plate 13. Outer petals—Cameo Pink, Plate 26, lightly overcast with Thulite Pink, Plate 26. Base of petals (aiglet)—Sea-Foam Green, Plate 31. Inside of petals—Thulite Pink, Plate 26. Reverse of petals—Rose Pink, Plate 12, lightly overcast with Cameo Pink, Plate 26. General tonality from a distance—Thulite Pink, Plate 26.
*Discoloration.*—General tonality at end of first day—Thulite Pink, Plate 26, very lightly overcast with Eugenia Red, Plate 13. Second day—Thulite Pink, Plate 26. Third day—Thulite Pink, Plate 26, lightly overcast with Cameo Pink, Plate 26.

Petals:
*Texture.*—Thin; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Slight. Nature—tea (average hybrid tea scent).
*Lasting quality.*—On the plant—long. As cut flower—long.

*Genital Organs*

Stamens, anthers: Small; few; regularly arranged around styles. Color—Orange-Buff, Plate 3.
Stamens, filaments (threads): Short. Color—Baryta Yellow, Plate 4.
Pollen: Color—Pale Yellow-Orange, Plate 3.
Styles: Uneven length; short; thin.
Stigmas: Color—Baryta Yellow, Plate 4.
Ovaries: All enclosed in calyx.
Hips: None.
Seeds: None.

*Plant*

Form: Bush.
Growth: Vigorous; dwarf; compact; height ranges from 8 to 10 inches.
Foliage: Compound of 3–5 leaflets.
*Size.*—Small.
*Quantity.*—Abundant.
*Color.*—New foliage: upper side—Absinthe Green, Plate 31; under side—Pale Olivine, Plate 32. Old foliage: upper side—Cress Green, Plate 31; under side—Kildare Green, Plate 31.
*Shape.*—Oval pointed.
*Texture.*—Upper side—leathery. Under side—smooth.
*Ribs and veins.*—Light.
*Edge.*—Serrated (saw-toothed).
*Serration.*—Single; small.

*Leaf stem.*—Color—Water Green, Plate 41. Under side—smooth.

*Stipules.*—Short; serrated.

Wood:

*New wood.*—Color—Light Turtle Green, Plate 32. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form—narrow base; short; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the miniature class, substantially as herein shown and described, characterized particularly as to novelty by the unique combination of a compact and miniature habit of plant growth, attractive foliage of Kildare Green color, and a distinctive and attractive general color tonality of the flowers corresponding to Thulite Pink.

No references cited.